(12) United States Patent
Fu et al.

(10) Patent No.: US 10,494,263 B2
(45) Date of Patent: Dec. 3, 2019

(54) METHOD FOR PREPARING BIOMASS GRAPHENE BY USING CELLULOSE AS RAW MATERIAL

(71) Applicants: JINAN SHENGQUAN GROUP SHARE HOLDING CO., LTD., Shandong (CN); Heilongjiang University, Heilongjiang (CN)

(72) Inventors: Honggang Fu, Heilongjiang (CN); Lei Wang, Heilongjiang (CN); Yilin Tang, Heilongjiang (CN); Jinzhu Zhang, Heilongjiang (CN); Yingfu Zheng, Heilongjiang (CN); Baojiang Jiang, Heilongjiang (CN)

(73) Assignees: HEILONGJIANG UNIVERSITY, Heilongjiang (CN); JINAN SHENGQUAN GROUP SHARE HOLDING CO, LTD, Shandong (CN)

( * ) Notice: Subject to any disclaimer, the term of this patent is extended or adjusted under 35 U.S.C. 154(b) by 329 days.

(21) Appl. No.: 15/555,289

(22) PCT Filed: Jan. 21, 2016

(86) PCT No.: PCT/CN2016/071540
§ 371 (c)(1),
(2) Date: Sep. 1, 2017

(87) PCT Pub. No.: WO2016/138802
PCT Pub. Date: Sep. 9, 2016

(65) Prior Publication Data
US 2018/0037460 A1    Feb. 8, 2018

(30) Foreign Application Priority Data

Mar. 4, 2015   (CN) .......................... 2015 1 0096254

(51) Int. Cl.
*C01B 32/184* (2017.01)
*B01J 27/043* (2006.01)
(Continued)

(52) U.S. Cl.
CPC ........... *C01B 32/184* (2017.08); *B01J 27/043* (2013.01); *B01J 27/26* (2013.01); *C08B 15/08* (2013.01); *G01N 21/65* (2013.01)

(58) Field of Classification Search
CPC ... C01B 32/184; C01B 32/182; C01B 32/198; C01B 2204/00; C01B 2204/02;
(Continued)

(56) References Cited

U.S. PATENT DOCUMENTS

2015/0307356 A1* 10/2015 Zhang ................... C01B 32/184
423/448
2017/0051078 A1* 2/2017 Tang ......................... D01F 2/08

FOREIGN PATENT DOCUMENTS

CN    101445234 A    6/2009
CN    101618870 A    1/2010
(Continued)

OTHER PUBLICATIONS

International Preliminary Report on Patentability issued in PCT/CN2016/071540, dated Sep. 5, 2017, 8 pages.
(Continued)

*Primary Examiner* — Daniel C. McCracken
(74) *Attorney, Agent, or Firm* — Faegre Baker Daniels LLP

(57) ABSTRACT

A method for preparing biomass graphene by using cellulose as a raw material includes preparing a catalyst solution, carrying out ionic coordination and high-temperature deoxidization on cellulose and a catalyst so as to obtain a precursor, carrying out thermal treatment and pre-carbonization, and carrying out acid treatment and drying to obtain
(Continued)

the graphene. The graphene is uniform in morphology with a single-layer or multi-layer two-dimensional layered structure having a dimension of 0.5 µm to 2 µm, and an electric conductivity of 25000 S/m to 45000 S/m. The graphene can be applied to electrode materials of super capacitors and lithium ion batteries, and can also be added to resin and rubber as an additive so as to improve physical properties of the resin and the rubber.

10 Claims, 2 Drawing Sheets

(51) Int. Cl.
    *B01J 27/26*     (2006.01)
    *C08B 15/08*     (2006.01)
    *G01N 21/65*     (2006.01)

(58) Field of Classification Search
    CPC ............ C01B 2204/04; C01B 2204/06; C01B 2204/065; C01B 2204/20; C01B 2204/22; C01B 2204/24; C01B 2204/26; C01B 2204/28; C01B 2204/30; C01B 2204/32; C01B 32/20; C01B 32/205; C01B 32/21; C01B 32/215; C01B 32/22; C01B 32/225; C01B 32/23; B01J 27/26; B01J 27/043; G01N 21/65; C08B 15/08
    See application file for complete search history.

(56) References Cited

FOREIGN PATENT DOCUMENTS

| | | | | | |
|---|---|---|---|---|---|
| CN | 103332684 | A | 10/2013 | | |
| CN | 103449399 | A | 12/2013 | | |
| CN | 103466613 | * | 12/2013 | ............ | C01B 31/04 |
| CN | 103466613 | A | 12/2013 | | |
| CN | 103935986 | A | 7/2014 | | |
| CN | 104016341 | * | 9/2014 | ............ | C01B 31/04 |
| CN | 104016341 | A | 9/2014 | | |
| CN | 104045077 | A | 9/2014 | | |
| CN | 104118873 | A | 10/2014 | | |
| CN | 104328523 | * | 2/2015 | ............ | C01B 31/04 |
| CN | 104328523 | A | 2/2015 | | |
| CN | 104724699 | A | 6/2015 | | |
| CN | 105060288 | A | 11/2015 | | |
| CN | 105502330 | A | 4/2016 | | |
| CN | 105502366 | A | 4/2016 | | |
| CN | 105504199 | A | 4/2016 | | |
| CN | 105504341 | A | 4/2016 | | |
| CN | 105504696 | A | 4/2016 | | |
| CN | 105504700 | A | 4/2016 | | |
| CN | 105506771 | A | 4/2016 | | |
| CN | 105524452 | A | 4/2016 | | |
| CN | 105525377 | A | 4/2016 | | |
| CN | 105525384 | A | 4/2016 | | |
| CN | 105603718 | A | 5/2016 | | |
| CN | 105623002 | A | 6/2016 | | |
| CN | 105800599 | A | 7/2016 | | |
| CN | 105800600 | A | 7/2016 | | |
| CN | 106243415 | A | 12/2016 | | |
| WO | 2017024933 | A1 | 2/2017 | | |
| WO | 2017063434 | A1 | 4/2017 | | |
| WO | 2017084542 | A1 | 5/2017 | | |
| WO | 2017084621 | A1 | 5/2017 | | |
| WO | 2017114174 | A1 | 7/2017 | | |
| WO | 2017121352 | A1 | 7/2017 | | |

OTHER PUBLICATIONS

International Search Report and Written Opinion with English Translations issued in PCT/CN2016/071540, dated Apr. 22, 2016, 17 pages.

Extended European Search Report issued in EP application No. 16758418.4, dated Jul. 20, 2018, 8 pages.

Sun, Li et al., "From coconut shell to porous graphene-like nanosheets for high-power supercapacitors," Journal of Materials Chemistry A, Apr. 3, 2013, 1, 6462-6470.

* cited by examiner

METHOD FOR PREPARING BIOMASS GRAPHENE BY USING CELLULOSE AS RAW MATERIAL

CROSS-REFERENCE TO RELATED APPLICATION

This application is a national phase application of PCT Application No. PCT/CN2016/071540, internationally filed Jan. 21, 2016, which claims priority to Chinese Application 201510096254.2, filed Mar. 4, 2015, all of which are herein incorporated by reference in their entirety.

TECHNICAL FIELD

The present disclosure relates to a method for preparing graphene, and particularly to a method for preparing biomass graphene using cellulose as a raw material.

BACKGROUND

Biomass is a natural cellulose raw material and is considered to be the most valuable and abundant renewable resource on the earth. In China, the annual yield of natural cellulose biomass is more than 700 million tons, of which corn cobs and stalks represent more than 30%. Biomass is rich in nutritional value and comprises useful chemical components. Although it is widely used in industry, agriculture and animal husbandry, more than 50% of the biomass is not being used. Presently in China, there is a lack of comprehensive measures in the efficient use of biomass such as corn cobs and stalks, often resulting in serious air pollution, which is also an important factor for frequent haze phenomenon and high concentration of fine particles smaller than particle pollution (PM) 2.5 in air. Although China is in the forefront of the world in the deep processing of biomass and has been successful in the exploitation, development and comprehensive utilization of plant stalks, if the use of biomass waste residue is unreasonable, secondary pollution will also be caused to the environment.

In recent years, graphene materials have a wider range of applications in the field of energy and environment, mainly because two-dimensional graphene has large specific surface area, excellent electronic conductivity, and can also be used as additives for resins and rubbers, which can improve physical properties of those materials to meet the needs in different areas. Currently, there are two mainly used methods for synthesizing graphene: chemical vapor deposition (CVD) and reducing graphite oxide. Graphene produced by the CVD method is suitable for use in electronic devices, but it usually requires harsh reaction conditions, expensive equipment, longer period, and has a lower yield, and thus CVD is not suitable for large-scale applications similar to those in the field of electrode materials. The reducing graphite oxide method requires an amount of strong oxidizing agent (e.g. concentrated sulfuric acid, potassium permanganate, etc.) which is roughly 12-fold the amount of the graphite raw material, resulting in serious environmental pollution. Production cost thereof remains high, thus greatly limiting the industrialization of the reducing graphite oxide method.

In summary, these existing graphene preparation methods have problems such as complicated process, poor production safety, high production cost, complicated reaction equipment, harsh reaction conditions, and low yield and others, making it difficult to achieve industrial production with existing methods. Accordingly, the present inventors have studied an alternative method capable of overcoming the above-mentioned obstacles and allowing the synthesis of high-quality biomass grapheneusing cellulose as a raw material that is low in cost, high in yield, high in production safety, highly controllable in the dimensions and physical properties of graphene, and more suitable for industrialized production than the existing methods.

SUMMARY

The objective of the present disclosure is to solve problems that the existing preparation methods for graphene have including complicated process, poor production safety, high production cost, complicated reaction equipment, harsh reaction conditions, and low yield.

A method for preparing biomass graphene using cellulose as a raw material, in accordance to various embodiments of the present disclosure, comprises the following steps:

Step 1: Preparation of a catalyst solution: a catalyst is added to distilled water and the mixture is stirred for 10-30 min to obtain a homogeneous catalyst solution, in which the ratio of solute to solvent is within the range of 2:100 to 35:100;

Step 2: Preparation of a precursor: biomass cellulose is added to the catalyst solution obtained in step 1, and the mixture is stirred for 1-4 h and then deoxidized at a high temperature and dried to obtain a precursor, in which the mass ratio of cellulose to solvent is within the range of 3:100 to 40:100;

Step 3: Heat treatment: pre-carbonization: the precursor obtained in step 2 is heated to 220-650° C. at a heating rate of 10-20° C./min in a nitrogen gas, argon gas or hydrogen gas atmosphere to be pre-carbonized for 1-6 h; secondary carbonization: the pre-carbonized product is heated to 900-1650° C. at a heating rate of 5-16° C./min for heat treatment for 4-15 h to carry out secondary carbonization treatment to the precursor obtained in step 2;

Step 4: Acid treatment, water-washing and drying: the product obtained in step 3 is acid-treated, centrifuged and then washed with distilled water to neutral, and then dried at 80-110° C. to obtain graphene.

Further, the cellulose is one or more types selected from the group comprising cellulose extracted from corncobs, corn stalks, sorghum stalks, soybean stalks, stems or leaves of cattail, coconut shells and palm shells.

Further, the catalyst in step 1 is one selected from the group comprising $FeCl_2$, $FeCl_3$, $K_3[Fe(CN)_6]$ and $K_4[Fe(CN)_6]$, or a mixture of more selected therefrom.

Further, in step 1, the stirring time is 13-25 min, and the ratio of solute to solvent in the catalyst solution is within the range of 3:100 to 25:100.

Further, in step 1, the stirring time is 15-20 min, and the ratio of solute to solvent in the catalyst solution is within the range of 4:100 to 15:100.

Further, in step 2, the stirring time is 2-3 h, and the deoxidation at a high temperature is conducted at a temperature of 110-205° C. for 6-16 h or at a microwave strength of 3-9 kW and a temperature of 110-170° C. for 5 min-2 h.

Further, in step 2, the deoxidation at a high temperature is conducted at a temperature of 120-180° C. for 8-12 h or at a microwave strength of 4-7 kW and a temperature of 130-160° C. for 20 min-1.5 h.

Further, in step 3, the pre-carbonation treatment is conducted under the following conditions: the precursor obtained in the step 2 is heated to 300-450° C. at a heating rate of 11-16° C./min and pre-carbonized for 2-5 h; the secondary carbonization treatment is conducted under the following conditions: the pre-carbonized product is heated to 1000-1550° C. at a heating rate of 5-12° C./min for heat treatment for 5-10 h.

Further, in step 3, the pre-carbonation treatment is conducted under the following conditions: the precursor obtained in the step 2 is heated to 330-420° C. at a heating rate of 12-16° C./min and pre-carbonized for 2-4 h; the secondary carbonization treatment is conducted under the following conditions: the pre-carbonized product is heated to 1050-1450° C. at a heating rate of 6-10° C./min for heat treatment for 5-8 h.

Further, in step 4, the acid used in the acid treatment is one or more selected from the group consisting of sulfuric acid, perchloric acid and nitric acid, and the temperature for drying is 90-105° C.

By utilizing cellulose extracted from a wide range of biomass sources as the inexpensive carbon source to produce graphene, reduction in production cost while increasing production can be realized. The yield of graphene is above 99%. Graphene with different properties can be obtained by changing the types of cellulose and catalyst and reaction conditions. Graphene prepared by the method of the present disclosure has a uniform size, a single layer or multi-layer two-dimensional layered structure, a size of 0.5-2 μm, and a conductivity of 25000-45000 S/m, and can be used in wider applications; it can be applied to fuel cell, oversized capacitors, fuel cells and other fields, and can also be used as additives for resin, rubber and others. In the present disclosure, the raw materials used are green and non-toxic, the reaction condition is mild, the production safety is high, and the industrial production is easy to be realized.

DESCRIPTION

Examples in accordance with the present disclosure will be described in detail below with reference to the accompanying drawings. It should be noted that technical features described in the following examples or combinations thereof should not be considered to be isolated, and instead they can be combined with each other to achieve the desired technical effects.

Figure 1:
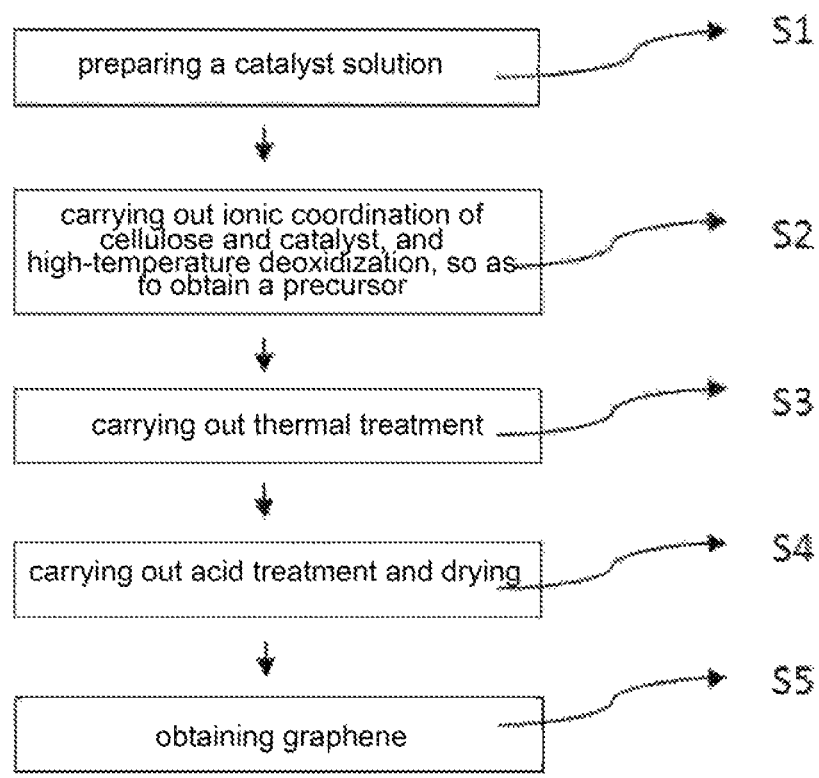
FIG. 1 is a diagram illustrating a method of preparing graphene, in accordance with various embodiments of the disclosure.

FIG. 1 is a diagram illustrating a method of preparing graphene, in accordance with various embodiments of the disclosure, comprises the following steps: S1 preparing a catalyst solution; S2: carrying out ionic coordination of cellulose and catalyst, and high-temperature deoxidization, so as to obtain a precursor; S3: carrying out thermal treatment; S4: carrying out acid treatment and drying; and S5: obtaining graphene.

Example 1

The present example for preparing biomass graphene using cellulose as a raw material is carried out by the following steps:

Step 1: Preparation of a catalyst solution: 18 g of $FeCl_2$ (solute) is added to 100 ml of distilled water (solvent) and the mixture is stirred for 25 min to obtain a homogeneous catalyst solution, in which the ratio of solute to solvent is 18:100;

Step 2: Preparation of a precursor: cellulose is added to the catalyst solution obtained in step 1, and the mixture is stirred for 2 h and then reacted for 10 h at a temperature of 140° C., then the mixture is deoxidized and dried to obtain a precursor, in which the mass ratio of cellulose to solvent is 26:100;

Step 3: Heat treatment: To pre-carbonize, the precursor obtained in step 2 is heated to 280° C. at a heating rate of 10° C./min in a nitrogen gas, argon gas or hydrogen gas atmosphere to be pre-carbonized for 3 h; To carry out secondary carbonization, the pre-carbonized product is heated to 1050° C. at a heating rate of 8° C./min for heat treatment for 6 h;

Step 4: Acid treatment, water-washing and drying: the product obtained in step 3 is acid-treated, centrifuged and then washed with distilled water to neutral, and then dried at 105° C. to obtain graphene.

Figure 2:
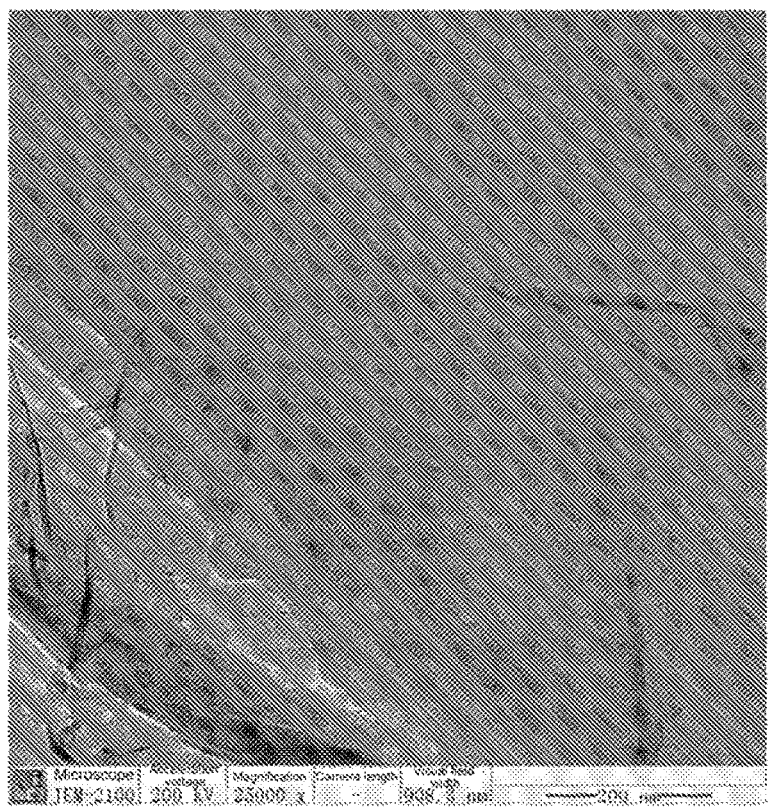
FIG. 2 is a transmission electron micrograph of graphene prepared according to Example 12.
Figure 3:
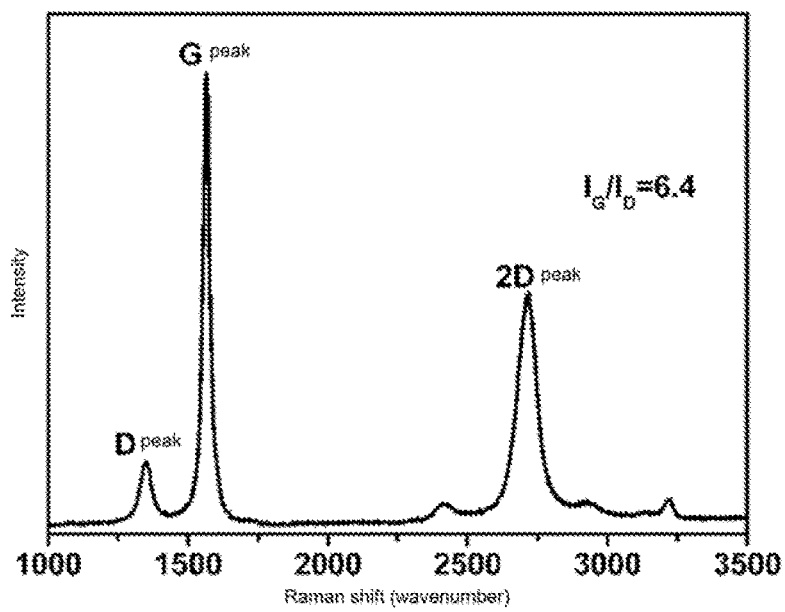
FIG. 3 is a Raman spectrum of graphene prepared according to Example 12.

The transmission electron micrograph of the graphene prepared in the present Example 1 is similar to that of Example 12, as shown in FIG. 2. The Raman spectrum of the graphene prepared in Example 1 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 2

This example differs from Example 1 in that the cellulose described in step 1 is cellulose extracted from soybean straw biomass.

The transmission electron micrograph of the graphene prepared in the present Example 2 is similar to that of Example 12, as shown in FIG. 2. The Raman spectrum of the graphene prepared in the present Example 2 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 3

This example differs from Example 2 in that the catalyst described in step 1 is a mixture of $FeCl_2$ and $FeCl_3$.

The transmission electron micrograph of the graphene prepared in the present Example 3 is similar to that of Example 12, as shown in FIG. 2. The Raman spectrum of the graphene prepared in the present Example 3 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 4

This example differs from Example 3 in that the deoxidation at a high temperature in step 2 is conducted at a temperature of 175° C. for 7 h or at a microwave strength of 4.5 kW and a temperature of 150° C. for 1 h.

The transmission electron micrograph of the graphene prepared in the present Example 4 is similar to that of Example 12, as shown in FIG. 2. The Raman spectrum of the graphene prepared in the present Example 4 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 5

This example differs from Example 4 in that the cellulose described in step 1 is cellulose extracted from sorghum stalk biomass.

The transmission electron micrograph of the graphene prepared in the present Example 5 is similar to that of Example 12, as shown in FIG. 2. The Raman spectrum of the graphene prepared in the present Example 5 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 6

This example differs from Example 5 in that the cellulose described in step 1 is cellulose extracted from the stems or leaves of cattail biomass.

The transmission electron micrograph of the graphene prepared in the present Example 6 is similar to that of Example 12, as shown in FIG. 2. The Raman spectrum of the graphene prepared in the present Example 6 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 7

This example differs from Example 6 in that the catalyst described in step 1 is $K_3[Fe(CN)_6]$.

The transmission electron micrograph of the graphene prepared in the present Example 7 is similar to that of Example 12, as shown in FIG. 2. The Raman spectrum of the graphene prepared in the present Example 7 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 8

This example differs from Example 7 in that the catalyst described in step 1 is $K_4[Fe(CN)_6]$.

The transmission electron micrograph of the graphene prepared in the present Example 8 is similar to that of Example 12, as shown in FIG. 2. The Raman spectrum of the graphene prepared in the present Example 8 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 9

This example differs from Example 8 in that the catalyst described in step 1 is $FeCl_2$.

The transmission electron micrograph of the graphene prepared in the present Example 9 is similar to that of Example 12, as shown in FIG. 2. The Raman spectrum of the graphene prepared in the present Example 9 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 10

This example differs from Example 9 in that the deoxidation at a high temperature in step 2 is conducted at a temperature of 160° C. for 9 h.

The transmission electron micrograph of the graphene prepared in the present Example 10 is similar to that of Example 12, as shown in FIG. 2. The Raman spectrum of the graphene prepared in the present Example 10 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 11

This example differs from Example 10 in that the deoxidation at a high temperature in step 2 is conducted at a microwave strength of 6 kW and a temperature of 135° C. for 0.5 h.

The transmission electron micrograph of the graphene prepared in the present Example 11 is similar to that of Example 12, as shown in FIG. 2. The Raman spectrum of the graphene prepared in the present Example 11 is similar to that of the graphene prepared in Example 12, as shown in FIG. 3.

Graphene prepared by the present example has a uniform size, a single layer or multi-layer two-dimensional layered structure, a size of 0.5-2 μm, and a conductivity of above 25000-45000 S/cm. The yield of graphene in this example is above 99.9%.

Example 12

The present example for preparing biomass graphene using cellulose as a raw material is carried out by the following steps:

Step 1: Preparation of a catalyst solution: 8 g of $K_3[Fe(CN)_6]$ catalyst is added to 125 g of distilled water and the mixture is stirred for 15 min to obtain a homogeneous catalyst solution;

Step 2: Preparation of a precursor: 17 g of cellulose extracted from sorghum stalks is added to the catalyst solution obtained in step 1, and the mixture is stirred for 3 h and then deoxidated at a microwave strength of 6 kW and a temperature of 140° C., and then dried to obtain a precursor;

Step 3: Heat treatment: To pre-carbonize, the precursor obtained in step 2 is heated to 350° C. at a heating rate of 12° C./min in a nitrogen gas atmosphere to be pre-carbonized for 2 h; For secondary carbonization, the pre-carbonized product is heated to 1050° C. at a heating rate of 6° C./min for heat treatment for 5 h;

Step 4: Acid treatment, water-washing and drying: the product obtained in step 3 is treated with nitric acid, centrifuged and then washed with distilled water to neutral, and then dried at 90° C. to obtain graphene.

FIG. 2 is a transmission electron micrograph of graphene prepared according to Example 12. It can be seen from the figure that the prepared product has a microstructure of two-dimensional layered shape and a size of about 700 nm. FIG. 3 is a Raman spectrum of graphene prepared according to Example 12, in which the G peak is higher than the D peak, the intensity ratio of the two peaks IG/ID=6.4, and a sharp 2D peak appears simultaneously, which further confirms the formation of graphene structure. The conductivity of the product is 32700 S/m, indicating that the graphene prepared by this method has good conductivity.

As can be seen from the above examples, cellulose extracted from biomass from a wide range of sources can be utilized inexpensively as a carbon source to produce graphene, and thus reduces production cost while increasing production. The yield of graphene is above 99%. Graphene with different properties can be obtained by changing the types of cellulose and catalyst and reaction conditions. Graphene prepared by the method of the present disclosure has a uniform size, a single layer or multi-layer two-dimensional layered structure, a size of 0.5-2 μm, and a conductivity of 25000-45000 S/m, and can be used in a wider applications; it can be applied to fuel cell, oversized capacitors, fuel cells and other fields, and can also be used as additives for resin, rubber and others. In the present disclosure, the raw materials used are green and non-toxic, the reaction condition is mild, the production safety is high, and the industrial production is easy to be realized.

Although some examples of the present disclosure have been presented herein, it will be understood by those skilled in the art that changes may be made in these examples without departing from the spirit of the disclosure. The above examples are illustrative only and should not be construed as limiting the claimed scope of the present disclosure.

The invention claimed is:

1. A method for preparing biomass graphene using cellulose as a raw material, comprising:

preparing a catalyst solution, wherein a catalyst is added to distilled water to form a first mixture, the first mixture is stirred for 10 to 30 min to form a catalyst solution, in which the ratio of catalyst to solvent is within 2:100 to 35:100;

preparation a precursor, wherein a biomass cellulose is added to the catalyst solution to form a second mixture, the second mixture is stirred for 1 to 4 hours then deoxidized at a high temperature and dried to obtain a precursor, in which the mass ratio of cellulose to solvent is within 3:100 to 40:100;

heat-treating the precursor including a pre-carbonization step and a secondary carbonization step, wherein the pre-carbonization step includes heating the precursor to within 220 to 650° C. at 10 to 20° C./min for 1 to 6 hours in an atmosphere including at least one of nitrogen gas, argon gas, and hydrogen gas to obtain a pre-carbonized precursor, and the secondary carbonization step includes heating the pre-carbonized precursor to within 900 to 1650° C. at 5 to 16° C./min for 4 to 15 hours to obtain a heat-treated product; and obtaining graphene, wherein the heat-treated product is acid-treated, centrifuged, washed with distilled water to neutral, and dried at 80-110° C. to obtain graphene.

2. The method of claim 1, wherein the biomass cellulose is at least one of cellulose extracted from corncobs, corn stalks, sorghum stalks, soybean stalks, stems or leaves of cattail, coconut shells, and palm shells.

3. The method of claim 1, wherein the catalyst is at least one of $FeCl_2$, $FeCl_3$, $K_3[Fe(CN)_6]$, and $K_4[Fe(CN)_6]$.

4. The method of claim 1, wherein the first mixture is stirred for 13 to 25 minutes, and the ratio of catalyst to solvent being within 3:100 to 25:100.

5. The method of claim 4, wherein the first mixture is stirred for 15 to 20 minutes, and the ratio of catalyst to solvent being within 4:100 to 15:100.

6. The method of claim 1, wherein the second mixture is stirred for 2 to 3 hours, and the deoxidation is conducted at one of 110 to 205° C. for 6 to 16 hours and 110 to 170° C. for 5 minutes to 2 hours at 3-9 kW in microwave strength.

7. The method of claim 6, wherein the deoxidation is conducted at one of 120 to 180° C. for 8 to 12 hours and 130 to 160° C. for 20 minutes to 1.5 hours at 4 to 7 kW in microwave strength.

8. The method of claim 1, wherein the pre-carbonization step includes heating the precursor to within 300 to 450° C. at 11 to 16° C./min for 2 to 5 hours, and the secondary carbonization step includes heating the pre-carbonized precursor to within 1000 to 1550° C. at 5 to 12° C./min for 5 to 10 hours.

9. The method of claim 8, wherein the pre-carbonization step includes heating the precursor to within 330 to 420° C. at 12 to 16° C./min for 2 to 4 hours, and the secondary carbonization step includes heating the pre-carbonized precursor to within 1050 to 1450° C. at 6 to 12° C./min for 5 to 8 hours.

10. The method of claim 1, wherein acid-treating is performed with acid comprising at least sulfuric acid, perchloric acid, and nitric acid, and drying is performed between 90 to 105° C.

* * * * *